CHRYSANTHEMUM PLANT
Filed July 30, 1974
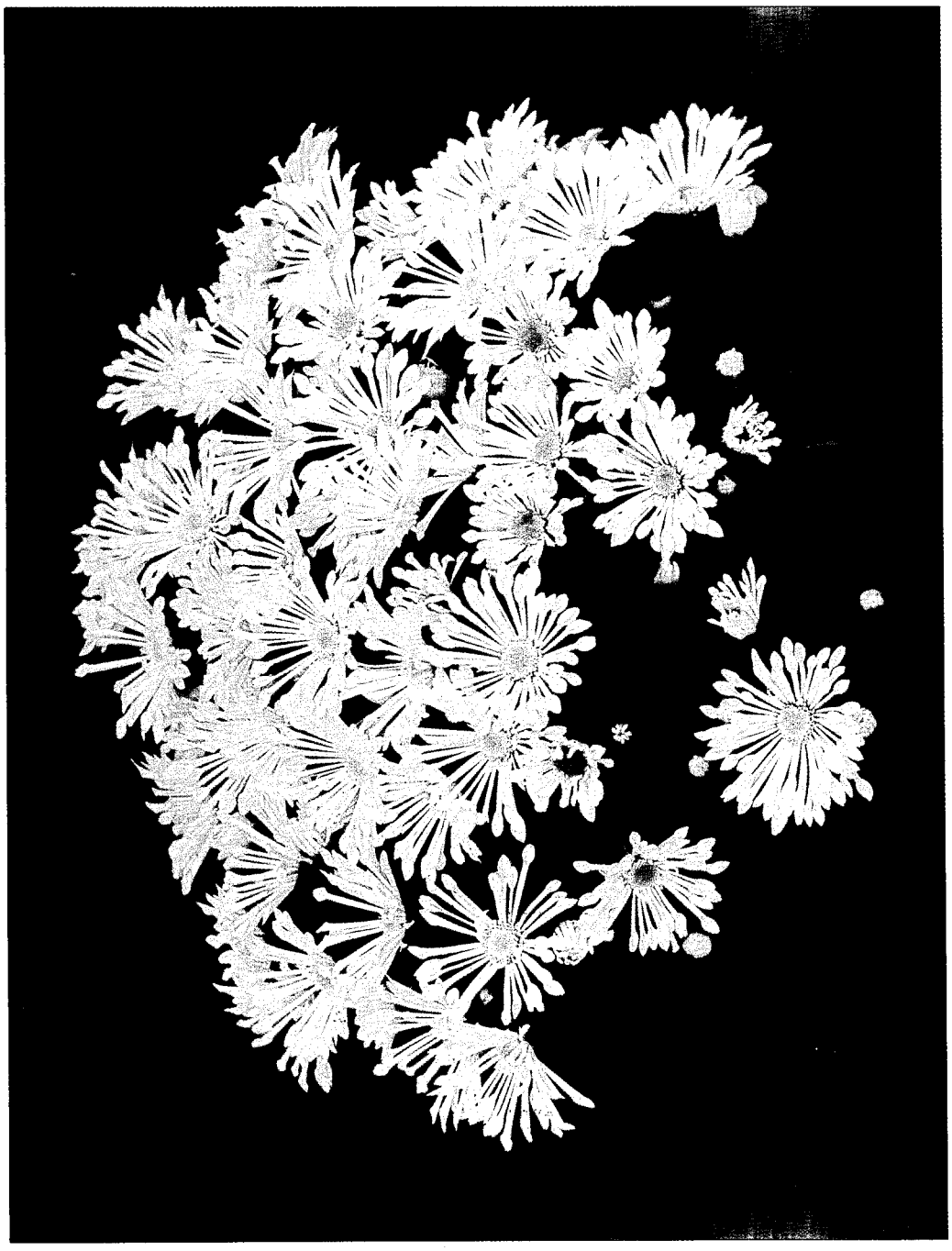

United States Patent Office

Plant Pat. 3,776

Patented Sept. 2, 1975

3,776
CHRYSANTHEMUM PLANT

Walter H. Jessel, Jr., Doylestown, and William E. Duffett, Akron, Ohio, assignors to Yoder Brothers, Inc., Barberton, Ohio

Filed July 30, 1974, Ser. No. 493,045

Int. Cl. A01h *5/00*

U.S. Cl. Plt.—74 1 Claim

The present invention comprises a new and distinct cultivar of chrysanthemum plant having the varietal name Sugar which is a seedling of #60228002, an unpatented cultivar known commercially by the varietal name Neptune, × #21670E02, disclosed in U.S. Plant Pat. No. 3,379, issued July 31, 1973, to John R. Culbert and known by the varietal name Illini Spinwheel. Both cultivars are identified for breeding purposes by the above breeding numbers.

The new cultivar is similar in many respects to Illini Spinwheel, having the same characteristics of:

1. Function as white spooned daisy for spray pot culture.
2. Petal form.
3. Adaptability to various pot sizes.
4. Breaking action and total flower production.
5. Sensitivity to aerosol and other oil base insecticides when applied under water stress and/or high temperature conditions.

The new cultivar is distinguished from Illini Spinwheel by the following characteristics when grown under comparable conditions:

1. A year round recommended period of value. Illini Spinwheel is only recommended for April through November flowerings in northern latitudes.
2. Flowers are approximately ½" to 1" larger in diameter.
3. Reduced pollen development and better flower form retention provides 5 to 7 days longer bench life, and 10 to 12 days longer home life.
4. Improved flower form retention. The spoon tip of the petal does not tilt down with age as is the case with Illini Spinwheel.
5. A whiter flower color with less ivory tones at all finishing temperatures.
6. Improved color clarity. Flowers do not pink with age or when finished at temperflatures less than 60° F.
7. A higher petal count. Sugar has approximately 20%–25% more petals per flower than Illini Spinwheel.
8. Will initiate and develop buds uniformly at temperatures as low as 52° F. Illini Spinwheel requires 60° F. for uniform bud initiation and development.
9. A greater tolerance to marginal low light conditions for uniform and efficient bud initiation. Illini Spinwheel does not initiate and develop buds as uniformly under similar conditions.
10. Approximately 3 to 5 days earlier flowering response.
11. A shorter, more controllable pot mum habit. Sugar requires short treatment year round. Illini Spinwheel should be grown on medium treatment which requires 1 less week of long days.

The new cultivar was selected from the progeny of the designated cross, and when asexually reproduced by cuttings at Barberton, Ohio, has been found to retain its distinctive characteristics through successive propagation.

The new cultivar, when grown in the vicinity of Barberton, Ohio, has a response period of approximately 8 weeks, and the following detailed description is based on observations made of the new cultivar in a greenhouse in Barberton, Ohio. The response time, blooming period, color, and total vigor may vary significantly with varying environmental conditions such as temperature, daylength, and light intensity. Suggested flowering in the northern United States, southeastern United States, southwestern United States, and coastal California is January through December, in southern Florida, under outdoor conditions, November through April.

The accompanying color photographic drawing shows the unique characteristics of the new cultivar, with the color being as nearly true as possible with color illustrations of this type.

In the following description, color references are made to the Munsell Book of Color, 1963 edition, and comparisons are made with the cultivar Illini Spinwheel. Where only a single value or description appears for the new cultivar Sugar, the same value of description applies as well to Illini Spinwheel.

Botanical classification: *Chrysanthemum morifolium*, Ramat.

| | Sugar | Illini Spinwheel |
|---|---|---|
| Bloom: | | |
| Size | 2¼" to 2½" | 1¾" to 2". |
| Fully expanded | 3¼" | 2¼". |
| Borne | In terminal clusters on elongated pedicels | |
| Stems | Strong and wiry | |
| Form | Spooned daisy | |
| Permanence | 14–20 days | 10–12 days. |
| Color: | | |
| Center of flower | Yellow-green, 2.5GY5/8 to yellow, 3.75Y8/12 | Yellow-green, 2.5GY6/10 to yellow, 3.75Y8/10; |
| Base of petals | Light yellow-green, 2.5GY7/10 | Yellow-green, 2.5GY8/10. |
| Inside of petals | Ivory white, 10Y9/1 to white, N9.5/ | Ivory, 10Y9/2 with tinges of pink, 5R5/8 under cool (less than 60° F.) finishes. |
| Reverse of petals | Ivory white, 10Y9/1 to white, N9/ | Ivory white, 10Y9/1. |
| Tonality from a distance | White | Ivory white. |
| Discoloration | White, N9.5/ | Ivory white, 10Y9/1 streaked pink, 5R5/8. |
| Petals: | | |
| Texture | Smooth | |
| Appearance and form | Tubular, flaring at tip, tapering to a blunt multi-notched tip. | |
| Arrangement | Composite, whorled on a single receptacle | |
| Persistence | Resists shatter | |
| Fragrance | Typical chrysanthemum | |
| Reproductive organs: | | |
| Stamen, anthers | 150–200 | |
| Pollen | Abundant to none (functional sterility) | |
| Arrangement | Clustered in center of flower if present | |
| Styles | Present both ray and disc florets | |
| Length | Short | |
| Ovaries | At the base of petal attached to receptacle | |
| Plant: | | |
| Form | Herbaceous | |
| Growth | Spreading | |
| Height | Approximately 11"–13" in a 4-cutting, 6" pot, grown as a spray pot given one 2,500 p.p.m. application of B-9 approximately 2 weeks after pinching and 8 week short treatment (2–3 weeks of long days) as defined in the timetables of Yoder Brothers, Inc., Barberton, Ohio, for the various seasons. | Approximately 11"–13" in a 4-cutting, 6" pot, grown as a spray pot given one 2,500 p.p.m. application of B-9 approximately 2 weeks after pinching and 9 week medium treatment (1–2 weeks of long days) as defined in the timetables of Yoder Brothers, Inc., Barberton, Ohio, for the various recommended seasons. |

| | Sugar | Illini Spinwheel |
|---|---|---|
| Spread | Approximately 7"–9" in a 4-cutting, 6" pot, grown as a spray pot given one 2,500 p.p.m. application of B-9 approximately 2 weeks after pinching and 8 week short treatment (2–3 weeks of long days) as defined in the timetables of Yoder Brothers, Inc., Barberton, Ohio, for the various recommended seasons. | Approximately 7"–9" in a 4-cutting, 6" pot, grown as a spray pot given one 2,500 p.p.m. application of B-9 approximately 2 weeks after pinching and 9 week medium treatment (1–2 weeks of long days) as defined in the timetables of Yoder Brothers, Inc., Barberton, Ohio, for the various recommended seasons. |
| Foliage: | | |
| Top side | Dark green, 7.5G Y3/4 | |
| Size | Length to width ratio 18:11 with length to 4½" and width to 2¾". | Length to width ratio 5:3 with length to 6½" and width to 3¾". |
| Quantity | Numerous | |
| Shape | Spatulate lobed | |
| Texture | Smooth | |
| Ribs and veins | Prominent | |
| Edge | Moderately indented | Deeply indented. |
| Serration | Deeply serrated | |
| Under side | Light greyed-green, 7.5G Y5/4 | |
| Stipules | Rudimentary | |

We claim:

1. A new and distinct cultivar of chrysanthemum of spooned daisy form characterized particularly as to uniqueness by its year round recommended period of value; flowers 2¼" to 2½" in diameter and 3¼" when fully expanded; reduced pollen development and excellent flower form retention, having a permanence of 14–20 days with no tilting down of the spoon tip with age; a white flower color and excellent color clarity, with no pinking with age or when finished at temperatures less than 60° F.; high petal count; by its ability to initiate and develop buds uniformly at temperatures as low as 52° F. and under marginal low light conditions; eight week response period, and by its controllable pot mum habit which requires short treatment year round.

No references cited.

ROBERT E. BAGWILL, Primary Examiner